United States Patent
McNary et al.

(10) Patent No.: US 7,156,827 B2
(45) Date of Patent: Jan. 2, 2007

(54) ADAPTER FOR LOCALIZED TREATMENT THROUGH A TRACHEAL TUBE AND METHOD FOR USE THEREOF

(75) Inventors: Richard McNary, Vernon, VT (US); Lawrence P. Hudon, Hinsdale, NH (US); Louis Woo, Arlington, VA (US); Roddi J. Simpson, Antrim, NH (US)

(73) Assignee: Smiths Medical ASD, Inc., Keene, NH (US)

( * ) Notice: Subject to any disclaimer, the term of this patent is extended or adjusted under 35 U.S.C. 154(b) by 640 days.

(21) Appl. No.: 10/419,820

(22) Filed: Apr. 22, 2003

(65) Prior Publication Data

US 2003/0216698 A1    Nov. 20, 2003

(51) Int. Cl.
*A61M 25/00*    (2006.01)
(52) U.S. Cl. ............... 604/264; 604/270; 604/284; 604/533; 128/200.26; 128/207.14; 128/207.16
(58) Field of Classification Search ........... 128/200.26, 128/206.28, 206.29, 207.14, 207.15, 207.16, 128/203.12, 912; 604/171, 264, 270, 523, 604/158, 109, 175, 174, 167.01, 910; 606/109
See application file for complete search history.

(56) References Cited

U.S. PATENT DOCUMENTS

| | | | |
|---|---|---|---|
| 3,739,778 A | 6/1973 | Monestere et al. | |
| 3,991,762 A | 11/1976 | Radford | |
| 4,240,417 A | 12/1980 | Holever | |
| 4,416,273 A | 11/1983 | Grimes | |
| 4,552,142 A | 11/1985 | Hoffman et al. | |
| 4,569,344 A | 2/1986 | Palmer | |
| 4,598,707 A | 7/1986 | Agdanowski et al. | |
| 4,838,255 A | 6/1989 | Lambert | |
| 4,850,350 A * | 7/1989 | Jackson ................ | 128/207.16 |
| 5,025,806 A | 6/1991 | Palmer et al. | |
| 5,073,166 A | 12/1991 | Parks et al. | |
| 5,158,569 A | 10/1992 | Strickland et al. | |
| 5,368,017 A * | 11/1994 | Sorenson et al. ...... | 128/200.26 |
| 5,419,314 A * | 5/1995 | Christopher ........... | 128/200.26 |

(Continued)

FOREIGN PATENT DOCUMENTS

WO    WO 95/08356    3/1995

*Primary Examiner*—Theresa Trieu
(74) *Attorney, Agent, or Firm*—Louis Woo

(57) ABSTRACT

By interposing an adapter between the endotracheal or tracheal tube inserted to a patient and the ventilation and suction systems that are connected to the endotracheal tube, a catheter could be inserted via an input port built into the adapter so as to enable a medical personnel to provide localized treatments in the lungs of a patient without having to disconnect either one of the systems connected to the endotracheal tube. The adapter is configured to have a securing mechanism that allows the medical personnel to secure the medication catheter in place. A one way valve fitted to the apertured arm that forms the input port of the adapter prevents any back flow of fluid from the input port. The catheter is manufactured with calibration markings, most likely equally spaced, and a radiopaque line along its length to enhance the maneuvering and the positioning thereof in the patient so that the distal tip of the catheter could be accurately positioned to the desired location of the patient's tracheal/bronchial tree. As a result, the localized treatment such as the injection of a medicament is accurately provided to the appropriate location where the need is the greatest.

6 Claims, 3 Drawing Sheets

U.S. PATENT DOCUMENTS

| | | |
|---|---|---|
| 5,460,613 A | 10/1995 | Ulrich et al. |
| 5,501,596 A | 3/1996 | Bailey |
| 5,642,726 A * | 7/1997 | Owens et al. ......... 128/200.26 |
| 5,653,230 A * | 8/1997 | Ciaglia et al. ......... 128/207.15 |
| 5,694,929 A * | 12/1997 | Christopher ........... 128/207.14 |
| 5,904,648 A | 5/1999 | Arndt et al. |
| 5,948,134 A | 9/1999 | Lee |
| 6,154,897 A | 12/2000 | Paini |

* cited by examiner

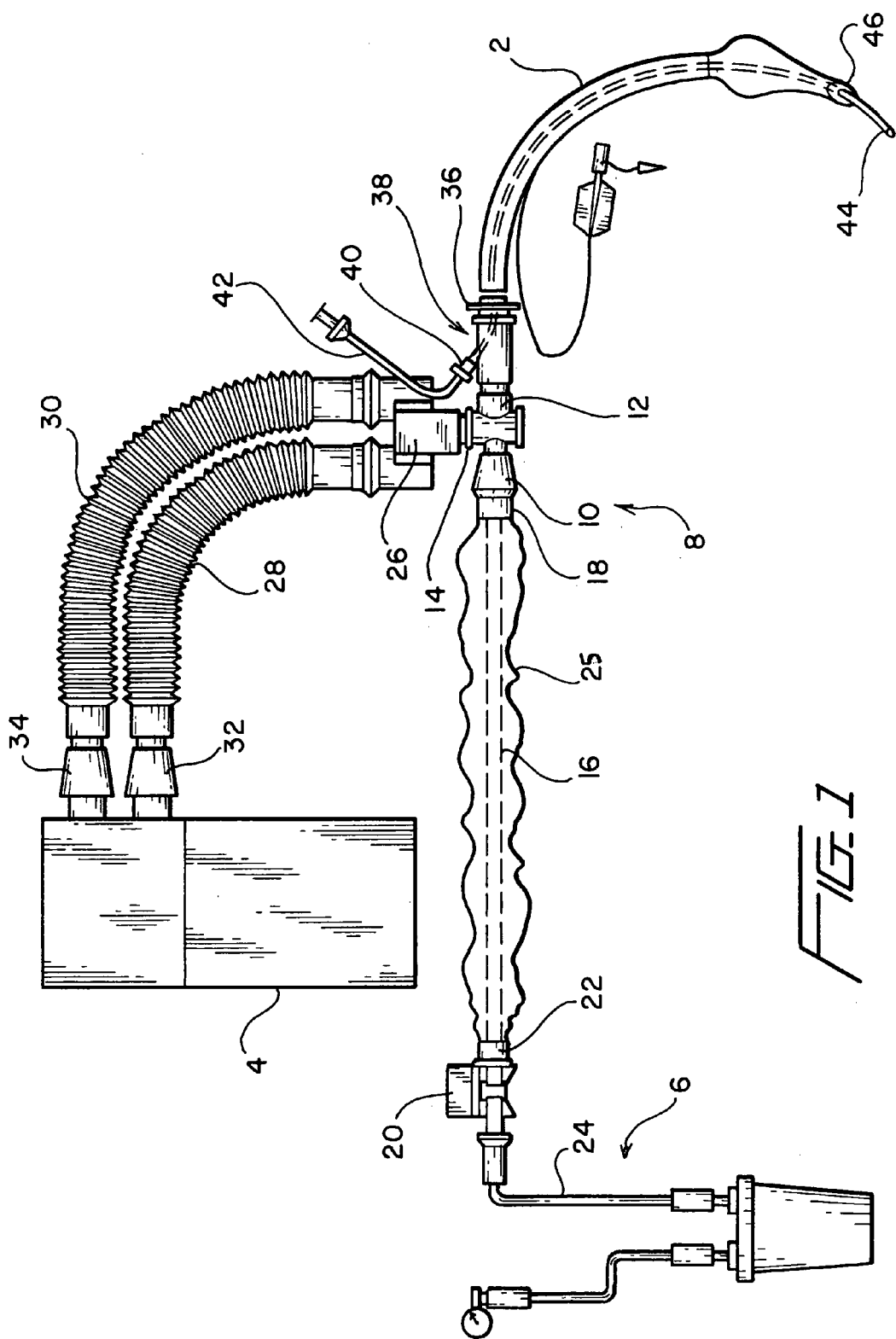

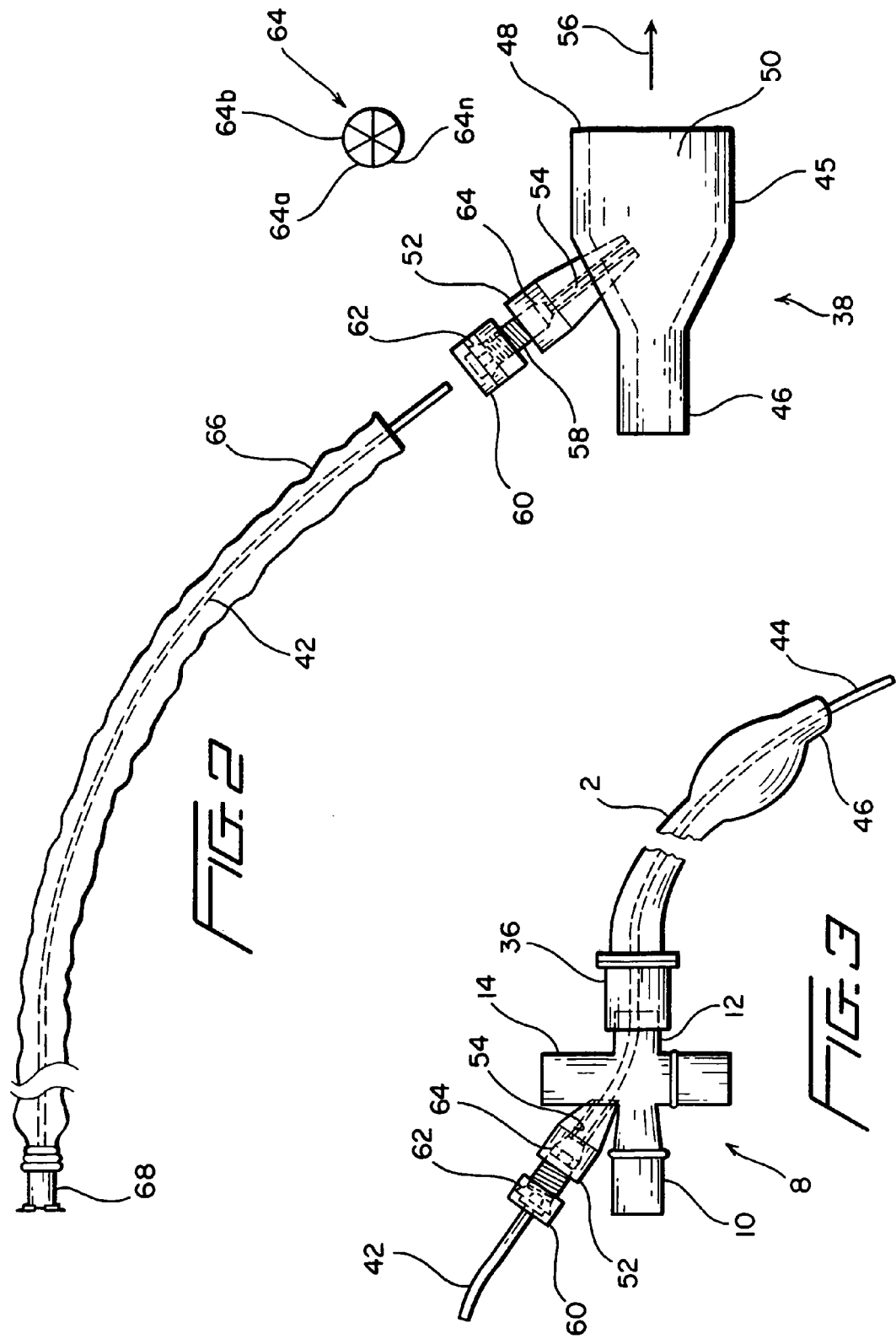

ADAPTER FOR LOCALIZED TREATMENT THROUGH A TRACHEAL TUBE AND METHOD FOR USE THEREOF

FIELD OF THE INVENTION

The present invention relates to the supplying of a medication and other fluids to a patient through either an endotracheal tube or a tracheal tube, and more specifically to the provisioning of an adapter to an endotracheal breathing circuit connected to the patient so that medication and/or other fluids such as oxygen may be provided to the lungs of the patient without having to disassemble the endotracheal breathing circuit.

BACKGROUND OF THE INVENTION

To enhance the breathing of a patient with a tracheal tube or an endotracheal tube, ventilation and suction systems are used. These systems are connected, by means of a connector, to the tracheal tube. (The term endotracheal tube henceforth should be taken to mean either an endotracheal tube or a tracheal tube.) The ventilation system provides ventilation to the patient while the suction system removes the fluids such as for example mucus secretions that accumulate in the trachea and the bronchi of the patient.

Oftentimes a patient connected to a tracheal tube has an acute lung injury. Consequently, medication must be provided to the patient. However, given that the endotracheal tube is connected in circuit with both the ventilator and the suction systems, prior to the instant invention, to supply medication to the patient, the systems, or at least one of the systems, connected to the patient's endotracheal tube has to be removed before medication may be supplied to the lungs of the patient. Needless to say, such removal and replacement of the ventilator and suction lines to the endotracheal tube is cumbersome, and oftentimes causes discomfort to the patient.

PCT publication WO95/08356 by the Assignee of the instant invention discloses the addition of an adapter in the ventilation circuit of the patient. The complete disclosure of the '356 publication is incorporated by reference to the disclosure of the instant application. The instant invention is an improvement of the adapter disclosed in the '356 publication. An alternative embodiment, as well as a method of using the same are also disclosed herein.

BRIEF DESCRIPTION OF THE PRESENT INVENTION

To ensure that a patient having an endotracheal tube inserted to his trachea is continuously connected to the ventilator and the suction system while medication is being provided, an adapter is interposed between the ventilator and the endotracheal tube of the patient. An input port is provided to the adapter so that a catheter that has calibration markings thereon and preferably a radiopaque line extending along its length is insertable to the adapter via the input port. To prevent back flow of fluids from the patient, fitted within the input port is a one way valve that opens only when the catheter is pressed thereagainst and subsequently passes therethrough. The input port, in conjunction with the adapter, would guide the catheter along the length of the endotracheal tube. The catheter is movable therealong until the distal end of the catheter extends beyond the distal end of the endotracheal tube.

With the aid of the equally spaced calibration markings and the radiopaque line along the catheter, the catheter may be accurately positioned to a desired location in the lungs of the patient. Once thus positioned, a medicament may be provided to the proximal end of the catheter, and be guided by the catheter to the desired location in the patient.

To regulate the length of the catheter inserted to the patient, a securing mechanism in the form of an internally threaded collar with extending fingers fitted thereto is threaded over the input port of the adapter, which in turn has at its upper arm an externally threaded portion that threadingly mates with the internal threads of the collar. When the collar is turned tightly on the arm of the input port, the fingers at the collar would compressively grasp the catheter, to thereby retain the catheter in place so that its distal end remains accurately positioned with respect to the desired location of the patient where the medication is to be supplied.

An alternative embodiment of the instant invention encompasses the incorporation of the adapter to the connector piece that acts as a junction for communicatively connecting the ventilator, the suction system and the endotracheal tube.

Instead of using the input catheter for supplying medication at the selected spot for the patient, the catheter may also be used for providing suction to a desired spot of the patient, by replacing the medicament supply means, such as for example a syringe or a medicament contained aerosol can, with a suction device. The suction device may be a part of the main suction provided to the endotracheal tube, or a distinct device that provides suction at the area where the tip of the catheter contacts.

In addition to using the catheter for supplying medicament to the patient and/or applying suction to a particular area such as for example the airways and/or lungs of the patient, other fluids or gases such as for example oxygen may be supplied through the catheter to the spot of the patient at the tip of the catheter, so that there is a high oxygenation directly at the desired patient location.

It is therefore an objective of the present invention to provide an adapter that allows medication to be provided to a patient fitted with an endotracheal tube without having to disassemble the ventilator and/or the suction system that are connected to the endotracheal tube.

It is also an objective of the present invention to provide an adapter that allows localized suction or oxygenation to a desired area of the patient fitted with an endotracheal tube without having to disassemble the ventilator and/or the suction system that are connected to the endotracheal tube.

It is another objective of the present invention to provide an improved multi-purpose adapter.

It is yet another objective of the present invention to incorporate an adapter to the main connector that jointedly connects the ventilator circuit, the suction circuit and the endotracheal tube.

BRIEF DESCRIPTION OF THE FIGURES

The above-mentioned objectives and advantages of the present invention will become apparent and the invention itself will best be understood with reference to the following description taken in conjunction with the accompanying drawings, wherein:

FIG. 1 is a schematic illustration of an overall view of the endotracheal tube being connected to a ventilator and a suction system, with the adapter of the instant invention being interposed between the endotracheal tube and the ventilator and suction system;

FIG. 2 is an illustration of the adapter of the instant invention, and its coaction and relationship with a catheter that is adaptable to be used for supplying localized medication, suction or oxygenation to a patient;

FIG. 3 is an illustration of an alternative embodiment of the adapter of the instant invention.

DETAILED DESCRIPTION OF THE PRESENT INVENTION

Figure 4:
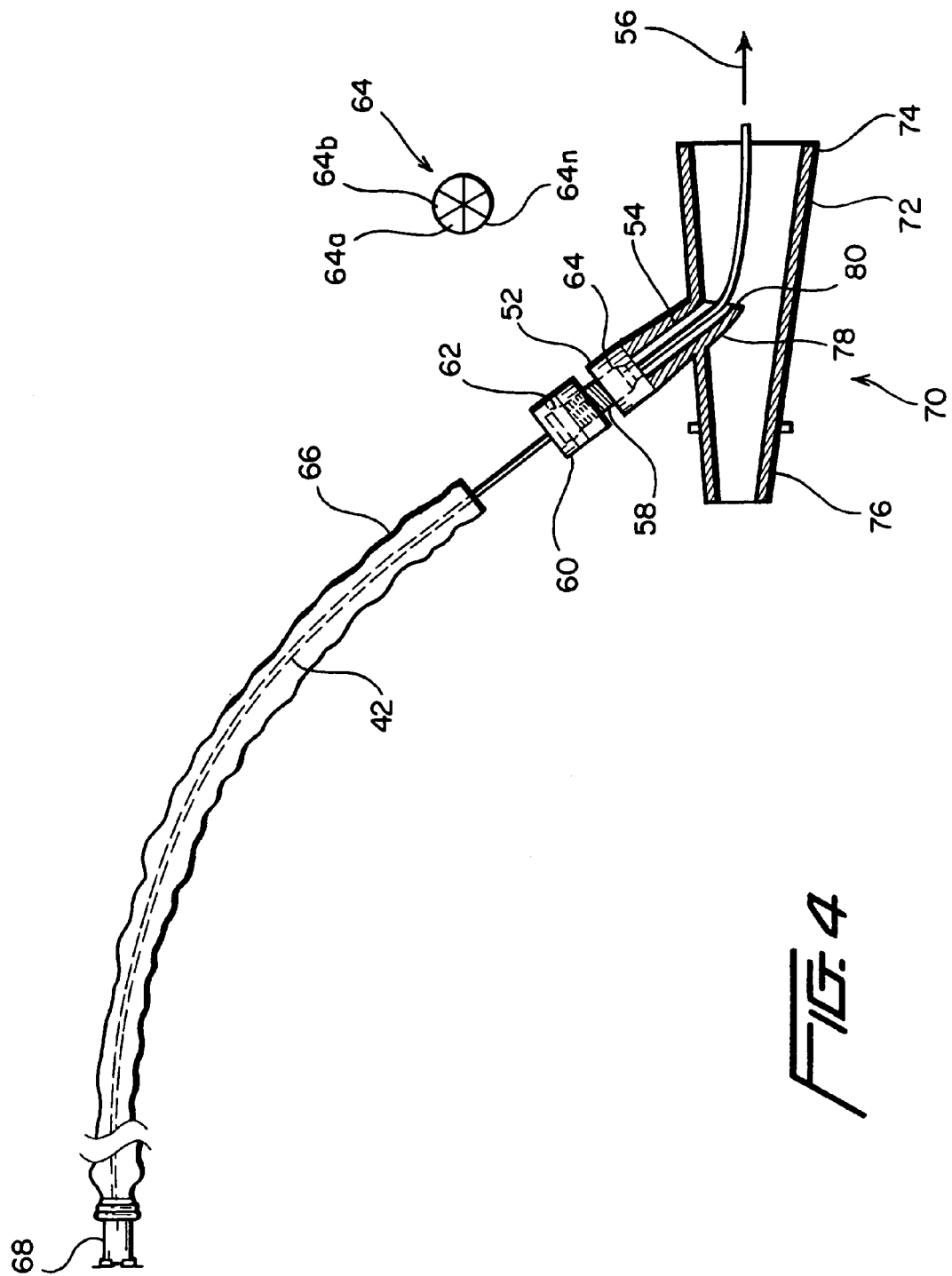
FIG. 4 is an illustration of an alternative embodiment of the adapter of the instant invention having an internal chute for guiding the movement of the catheter.

With reference to FIG. 1, an overall illustration of the interconnections of an endotracheal tube, a ventilator system, a suction system, and the instant invention adapter is shown. In particular, an endotracheal tube or a tracheal tube 2 is shown to be in communication with a ventilator 4 and a suction system 6. The communications among endotracheal tube 2, which is inserted into a patient (not shown for the sake of simplicity), ventilator 4 and suction system 6 are established by means of a junction connector 8. As shown, junction connector 8 is cross shaped and has a first leg 10, a second leg 12 and a third leg 14. Additional legs, not shown, may also be incorporated to connector 8.

Leg 10 is coupled to a suction catheter 16 by means of an appropriate coupler such as 18. The other end of suction catheter 16 is connected to a control valve mechanism 20, by way of a coupler 22. Control valve mechanism 20 is connected to a vacuum line 24, that in turn is connected to a conventional vacuum source usually built into the wall of the room of the patient. Enclosing suction catheter 16 is a protective sleeve 25, which collapses when suction catheter 16 is inserted through endotracheal tube 2 to the trachea/bronchial tree of the patient for removing fluids collected thereat by way of suction.

Connected to leg 14 of junction connector 8 is a coupler 26 that is connected to the distal ends of two flexible conduits 28 and 30. The respective proximal ends of conduits 28 and 30 are connected, by corresponding couplers 32 and 34, to ventilator 4. The combination of conduits 28, 30 and ventilator 4 could be considered as a ventilator circuit that mechanically pumps and removes air to the patient. Such ventilator circuit for ventilating a patient is conventional.

Interposed between leg 12 of cross connector 8 and the proximal end 36 of endotracheal tube 2 is an aperture adapter 38 of the instant invention. As shown in FIG. 1, adapter 38 has an input port 40 that allows a medication catheter 42 to be inserted to endotracheal tube 2 so that its distal end 44 could be moved along the length of endotracheal tube 2 and eventually extended beyond tip 46 thereof. Medication catheter 42 can then be maneuvered to a desired location at the trachea/bronchial tree of the patient. Once positioned at the desired location, a medicament such as for example recombinant surfactant protein C (rSPC surfactant), also know as "venticute", could be supplied to that desired location of the trachea/bronchial tree of the patient.

To enhance its movement along the length of endotracheal tube 2 and inside the patient, medication catheter 42 has along its length calibrated markings that allow a user to readily gauge the length of the catheter that has been inserted to the patient. To further enhance the maneuvering of medication catheter 42, a radiopaque line is integrated along substantially its entire length.

FIG. 2 provides an enlarged view of adapter 38 of FIG. 1. In particular, adapter 38 has a main body 45 having a proximal end 46 that is matingly coupled to leg 12 of cross connector 8. Distal end 48 of adapter 38, on the other hand, is matingly coupled to connector 36 of endotracheal tube 2. Adapter 38 is hollow so that a fluid path 38 is created along its length to enable free passage of suction catheter 16, as well as bidirectional passage of air from the ventilator circuit.

At a side of body 38 there is fitted an apertured arm or extension 52. Apertured arm 52 thus provides an input port to adapter 38. Aperture 54 in arm 52 has a sufficient dimension to allow medication catheter 42 to pass therethrough. Arm 52 is incorporated or fitted to body 38 at an angle relative to the longitudinal axis of body 45, so as to enable catheter 42, once inserted to arm 52, to pass therealong and be routed along the direction as indicated by directional arrow 56.

Arm 52 has a top portion 58 that is externally threaded. An internally threaded collar 60 is threadingly mated to portion 58 of arm 52. Collar 60 is moreover internally fitted with a number of fingers 62, better shown in FIG. 3, that are compressible toward each other when collar 60 is threaded onto portion 58. The relationship of fingers 62 with medication catheter 42 is such that once catheter 42 is inserted to arm 52, upon collar 60 being fully threaded onto portion 58, fingers 62 would compress in unison onto the outer surface of catheter 42, without occluding catheter 42, at the location where it makes contact with fingers 62, so that catheter 42 is grasped by fingers 62 and be fixedly retained in position.

Further fitted to arm 52 is a one way valve 64 such as for example a duck bill valve. As shown by its enlarged planar view, one way valve 64 has a number of pliable flaps or portions 64a–64n that have sufficient elasticity so as to open just enough to enable catheter 42 to pass therethrough, and yet nonetheless would prevent any fluid in path 50 from flowing backwards out of arm 52. Upon removal of catheter 42 from arm 52, pliable portions 64a–64n would return to their respective original positions to act as a stop to prevent any back flow of fluids from the patient. For the illustration in FIG. 2, pliable portions 64a–64n could be considered to be opened along the direction into the paper.

FIG. 3 is an alternative embodiment of the instant invention in which apertured arm 52 is integrated directly to cross connector 8. Arm 52 is integrated to connector 8 at an appropriate angle so that catheter 42 could easily be inserted into endotracheal tube 2. All components discussed above with reference to arm 52 in FIG. 2 are present in the embodiment shown in FIG. 3.

FIG. 4 illustrates an alterative embodiment of the adapter of the instant invention in which a guide means in the form of an elbow or a chute internal of the adapter housing is provided for guiding the catheter towards the center of the housing when the catheter is inserted to the adapter. Except for the adapter and the guide means internal thereof, all components which are the same or function the same as previously discussed are designated with the same numbers.

In particular, adapter 70 of the FIG. 4 embodiment could be considered as a connector means that has a main body 72. Although shown as a somewhat gradually increasing diameter cylindrical body, it should be appreciated that body 72 of adapter 70 could in fact be configured to have different shapes. As was the case with the previously discussed adapter, distal end 74 of housing 72 is used to mate with an endotracheal tube while the proximal end 76 of housing 72 is connectable to a suction catheter. As was the case in the embodiment shown in FIG. 2, aperture arm 52 provides an input port to adapter 70.

However, for the embodiment as shown in FIG. 4, a guide means in the form of an elbow 78 is integrated to the interior surface of housing 72 so as to extend from aperture arm 52. Elbow 78 is configured such that it provides a surface that guides catheter 42 into body 72 in such a way that once inserted beyond the mouth of elbow 78, as indicated at 80, further extension of catheter 42 would move catheter 42 into and substantially along the longitudinal axis of housing 72, so as to enhance the insertion of catheter 42 to the endotracheal tube. Elbow 78 therefore acts as a means to enhance the insertion and guide the movement of catheter 42 into adapter 70 and then the endotracheal tube. Needless to say, it also enhances the insertion of the catheter to the desired area of the lungs of the patient along the direction indicated by arrow 56.

In operation, medication catheter 42, which is enveloped by a protective sleeve 66 as shown in FIG. 2, is inserted to aperture arm 52 by way of collar 60, which has an opening, not shown, that matches aperture 54 of arm 52. As the distal tip 44 of catheter 42 makes contact with the pliable fingers 64a–64n of fitting 64, it pushes the pliable fingers 64 in a direction toward connector 8 so that an opening is formed to enable catheter 42 to pass therethrough. By reading the calibrated markings along catheter 42, the length of catheter 42 that is being inserted to arm 52, and subsequently to endotracheal tube 2, is readily determined. And with the length of catheters 42 and the combined distances or lengths of arm 52, connector 8 or body 45 (the FIG. 2 adapter), and endotracheal tube 2 known, the user can readily determined when distal tip 44 of catheter 42 is extended beyond tip 46 of tracheostomy tube 2.

Further, with the radiopaque line incorporated along substantially its entire length, catheter 42 could be readily maneuvered to precisely position its distal tip 44 to the appropriate location in the lung of the patient. Thereafter, a medicament container such as for example a syringe is inserted to the input 68 at the proximal end of catheter 42. By pushing in the plunger of the syringe, the medicament such as for example the venticute as mentioned previously is squirt into catheter 42 and conveyed therealong to output, at distal tip 44, to the desired location in the lung of the patient. Thus, given that the medicament is applied to substantially the desired precise location, a smaller dose of the medicament would achieve the same result as the larger doses in the prior art. Moreover, the medicament is concentrated in the particular area of need and therefore would act more quickly as compared to the prior art methods of non-localized application of the medicament.

Although catheter 42 as disclosed above has been described as a guide for inputting medicament to a desired location of the lungs of a patient, the fact that catheter 42, in most instances, is smaller in diameter and easier to maneuver than suction catheter 16 means that catheter 42 could be more accurately placed and positioned adjacent to a desired area in the tracheal/bronchial tree of a patient. Catheter 42 could also be used for suctioning a particular location in the bronchial tree of the patient. This is done either by configuring another flexible conduit from ventilator 4 that is matable with input 68 of catheter 42. An alternative is to have a suction device, independent of ventilator 4, that has an output that is matable with input 68 at the proximal end of catheter 42 to apply a suction force to catheter 42 for suctioning fluid collected at the selected area of the bronchial tree of the patient. This dual use of catheter 42, i.e., suctioning as well as providing medicament to the desired area of the patient, could be done with the same catheter. For example, it could very well be that it is desirable to suction out whatever fluid that has been collected in a certain area of the lungs of the patient before medicament is supplied thereto. The fact that the same catheter could be used for both functions means that there is only need to insert a single catheter into the lung of the patient. The fact that catheter 42 has calibrated markings along its length and a radio opaque line along the length thereof means that it could be readily maneuvered to the desired location for application of either the medicament or suction.

In addition to the application of medicament and suction, catheter 44 could also be used for a number of other things, if the application of a certain desired result is aimed at a precise location in the lungs of the patient. For example, in place of a medicament, oxygen may be fed by means of the catheter to the desired site, so that a high or concentrated oxygenation may be applied to the chosen site at the lungs of the patient in order to achieve faster result. An oxygen supply may be provided by an oxygen flow meter that has an output which is configured to fit to input 68 of catheter 42.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

The invention claimed is:

1. A method of directing localized treatment to the lungs of a patient through an endotracheal or tracheal tube having a distal end inserted to the patient, said tube having communicatively connected thereto a suction line and a ventilation line via a connector means, the method comprising the steps of:

integrating to said connector means an input port independent of said suction line and said ventilation line;
mounting to the proximal end of said input port a securing means;
fitting within said input port a one way valve;
inserting a catheter having a distal end to said input port;
moving said catheter to open said one way valve;
extending said catheter pass said one way valve through said connector means to said tube;
moving said catheter along said tube until the distal end of said catheter extends beyond the distal end of said tube;
locating the distal end of said catheter to a desired location in the lungs or the bronchial tree of the patient; and
guiding via said catheter the localized treatment to said desired location in the lungs or the bronchial tree of the patient.

2. Method of claim 1, wherein said locating step further includes the steps of:

adding markings along the length of said catheter;
adding a radiopaque line along the length of said catheter; and
utilizing said markings and said radiopaque line along the catheter to position said catheter inside the patient.

3. Method of claim 1, further comprising the steps of:

providing an elbow means extending from said input port internal of said connector means; and
configuring said elbow means to guide the movement of said catheter as said catheter is moved along said connector means to ensure that said catheter is moved substantially along the center of said connector means for insertion to said tube.

4. Method of claim 1, wherein the localized treatment comprises the step of:

injecting a medicament to the proximal end of said catheter so that said medicament is guided by said catheter to said selected location in the lungs or the bronchial tube of the patient.

5. Method of claim 1, wherein the localized treatment comprises the step of:

inputting oxygen to the proximal end of said catheter so that said catheter guides the oxygen to oxygenate said selected location in the lungs or the bronchial tube of the patient.

6. Method of claim 1, wherein the localized treatment comprises the step of:

connecting a vacuum source to the proximal end of said catheter to effect localized suction at said selected location in the lungs or the bronchial tube of the patient.

* * * * *